United States Patent [19]

Savins

[11] 4,006,058
[45] Feb. 1, 1977

[54] BIOPOLYMER PRODUCTION PROCESS
[75] Inventor: Joseph George Savins, Dallas, Tex.
[73] Assignee: Mobil Oil Corporation, New York, N.Y.
[22] Filed: Nov. 24, 1975
[21] Appl. No.: 634,986
[52] U.S. Cl. ............................... 195/49; 195/31 P; 195/100; 195/114
[51] Int. Cl.² ......................................... C12D 13/04
[58] Field of Search ........... 195/31 P, 49, 114, 100, 195/99, 101, 102, 103, 118, 124

[56] References Cited
OTHER PUBLICATIONS

Martin; John Charles, "Batchwise Production of Biopolymer from Methanol Fermentation", Jan. 1974 (Master Thesis) Cornell University.

Primary Examiner—A. Louis Monacell
Assistant Examiner—Thomas G. Wiseman
Attorney, Agent, or Firm—C. A. Huggett; William D. Jackson

[57] ABSTRACT

An improved process for the production of a heteropolysaccharide by fermentation of a methanol containing culture medium with a microorganism of *Methylomonas mucosa* NRRL B-5696 wherein an alkali metal glycerophosphate is incorporated into the culture medium to provide a source of assimilable phosphate. An iron chelating agent selected from the group consisting of the alkali metal and the ferric/alkali metal salts of ethylenediaminetetraacetic acid may be added to the culture medium and N-tris(hydroxymethyl)-methyl glycine may be employed as a buffering agent. The heteropolysaccharide thus produced may be employed in the in vivo form to provide a viscous aqueous solution injected into a subterranean oil reservoir for mobility control purposes.

11 Claims, No Drawings

BIOPOLYMER PRODUCTION PROCESS

BACKGROUND OF THE INVENTION

This invention relates to the production of bipolymers and more particularly to an improved process for the production of a heteropolysaccharide by action of a microorganism of the species *Methylomonas mucosa*.

U.S. Pat. No. 3,878,045 to Tannahill et al. discloses a method of preparing a biopolymer by the culturing of a heteropolysaccharide producing strain of the species *Methylomonas mucosa* in an aqueous culture medium containing methanol. The Tannahill et al. patent refers to application Ser. No. 364,559, filed May 29, 1973, now U.S. Pat. No. 3,923,782 by Finn et al. for a description of the heteropolysaccharide and its method of preparation. The biopolymer and its preparation are also disclosed in the Masters Theses presented to the faculty of the Graduate School of Cornell University by Joseph Edward Laptewicz, Jr., August 1972, entitled "BIOPOLYMER FROM A METHANOL-UTILIZING BACTERIUM" and by John Charles Martin, January 1974, entitled "BATCHWISE PRODUCTION OF BIOPOLYMER FROM METHANOL FERMENTATION".

As disclosed in the Tannahill et al. patent, the culture medium contains inorganic salts providing sources of phosphate, nitrate, sulfate, iron, calcium, magnesium, and zinc. Phosphate is added to the medium in the form of monobasic potassium phosphate and dibasic sodium phosphate. The desirability of maintaining adequate levels of soluble iron for biomass and biopolymer production is recognized by the patentees. Thus they suggest the use of various chelating agents such as ethylenediaminetetraacetic acid in order to enhance the availability of the iron for action by the microorganism. Tannahill et al. also disclose that the pH of the culture medium should be controlled within a relatively narrow range. The patentees indicate that no growth occurs at pH levels below 5.7 or above 8.0 and that a pH range of about 6–7.8 is preferred for growth of the microorganism.

SUMMARY OF THE INVENTION

In accordance with the present invention, there is provided a new and improved process for the production of a heteropolysaccharide by fermentation of a methanol containing culture medium with a microorganism of the strain *Methylomonas mucosa*, in particular the isolate identified as No. NRRL B-5696 (USDA, Northern Regional Research Laboratory, Peoria, Ill.). This improvement comprises incorporating into the culture medium an alkali metal salt of glycerophosphoric acid to provide a readily assimilable source of phosphate. The alkali metal glycerophosphate is the predominant source of the assimilable phosphate in the culture medium and preferably is present in an amount within the range of 0.3–3.0 weight percent.

In a further embodiment of the invention there is incorporated into the culture medium a chelating agent for iron selected from the group consisting of the alkali metal salts and mixed ferric/alkali metal salts of ethylenediaminetetraacetic acid. In a still further improvement, tricine, N-tris-(hydroxymethyl)methyl glycine, is employed in the culture medium as a hydrogen-ion buffer.

DESCRIPTION OF SPECIFIC EMBODIMENTS

The microorganism employed in the present invention is a bacterium of the species *Methylomonas mucosa* and identified by Deposit No. NRRL B-5696, USDA. Its mycological characteristics, including the cultivation procedure, are disclosed in the aforementioned patent to Tannahill et al. to which reference is made for a more detailed description.

As disclosed in the Tannahill et al. patent, the biopolymer is a viscosity enhancing agent in an aqueous medium and thus has utility in various applications such as a drag reducing agent in aqueous liquids and as a thickening agent for use in foods, cosmetics, paints, and drilling muds. A particularly important use ascribed to the biopolymer is in the recovery of oil from subterranean oil reservoirs by waterflooding. The biopolymer may be added to water injected into a subterranean oil reservoir to form a thickened aqueous slug for mobility control purposes. For a further description of mobility control in the recovery of oil by waterflooding, reference is made to a paper by W. R. Foster entitled "A Low-Tension Waterflooding Process", Journal of Petroleum Technology, Vol. 25, Feb. 1973, pp. 205–210.

A typical broth medium disclosed in Tannahill et al. for growth of the microorganism *Methylomonas mucosa* contains the following inorganic salts in the minimum amounts and order of addition indicated:

TABLE I

| Material | Grams per Liter |
| --- | --- |
| $KH_2PO_4$ | 3.75 |
| $Na_2HPO_4$ | 2.50 |
| $NaNO_3$ | 2.50 |
| $MgSO_4 . 7H_2O$ | 0.40 |
| $Ca(NO_3)_2 . 4H_2O$ | 0.005 |
| $FeSO_4 . 7H_2O$ | 0.005 |
| or | |
| $Fe(NH_4)_2(SO_4)_2 . 6H_2O$ | 0.007 |
| $ZnSO_4 . H_2O$ | 0.005 |

The methanol substrate is employed in an amount within the range of about 0.5–5.0 percent by volume. As noted in Tannahill et al., two different orders of addition of methanol may be employed. In one case, the entire amount of methanol employed is added to the culture medium at the outset of the fermentation procedure. In the improved process specifically disclosed in the Tannahill et al. patent, fermentation is initiated with only a portion of the methanol requirement present in the culture medium and then the remainder of the methanol requirement is added to the culture medium at one or more times during the fermentation period. The initial concentration of methanol is within the range of 0.5–2 volume percent with about 1–4 volume percent of methanol added subsequently. The patentees disclose that by employing this sequential order of methanol addition, broth viscosities may be increased tenfold or more over the procedure in which the total methanol requirement is added at the initiation of the fermentation procedure.

In accordance with the present invention, a higher viscosity yield and improved viscosity kinetics are obtained by employing in the culture medium an alkali metal glycerophosphate which provides a source of assimilable phosphate. The alkali metal glycerophosphate may be employed in the culture medium in addition to other phosphate sources such as the potassium and sodium phosphates disclosed in Table I or it may be substituted for these salts and thus provide the sole source of assimilable phosphate in the culture medium. It is preferred to employ the alkali metal glycerophosphate as the sole source or at least the predominant source of assimilable phosphate in the culture medium in order to guard against loss of essential nutrients from the formation of undesirable precipitates, and to minimize pH variations attendant to the use of inorganic salts such as the aforementioned potassium and sodium phosphates.

While any alkali metal glycerophosphate may be used in carrying out the invention, sodium glycerophosphate is preferred because of its commercial availability. This material is easily incorporated into the culture medium and readily assimilated by the microorganism to provide the phosphate needed for synthesis of biomass and biopolymer. Normally it will be preferred to employ the sodium glycerophosphate in an amount within the range of 0.3-3.0 weight percent. An especially suitable phosphate source is the disodium pentahydrate ($\alpha$ and $\beta$ mixture) of glycerophosphate.

In a further improvement in accordance with the present invention, a chelating agent for iron is employed which is selected from the group consisting of alkali metal salts of ethylenediaminetetraacetic acid and mixed ferric/alkali metal salts of ethylenediaminetetraacetic acid. By employing these salts rather than the acid form, the tendency to experience undesirable variations in pH is alleviated. In addition through the use of the mixed ferric/alkali metal salts the presolubilized, complexed iron is provided in the culture medium where it may be readily assimilated by the microorganism. While any alkali metal salt of ethylenediaminetetraacetic acid may be employed as the chelating agent, the tetrasodium salt or the mixed ferric/sodium salt of ethylenediaminetetraacetic acid normally will be preferred. The chelating agent may be employed in the culture medium in an amount within the range of 1-200 weight parts per million (0.0001-0.02 weight percent). The chelating agent normally is added to the culture medium with the inorganic iron salt.

As noted previously, it is desirable to maintain the pH of the culture medium within specified limits during the fermentation process. Although polysaccharide production is obtained at pH values within the range of 6-8, the aforementioned Tannahill et al. patent suggests that optimum growth occurs at a pH of about 7. The pH variations about this level may be minimized through the use of the aforementioned sodium glycerophosphate in place of the inorganic phosphates, particularly the dibasic sodium phosphate which can raise the pH of the culture medium to significant alkaline levels. In accordance with the present invention, a further improvement in this regard is effected through the use of an organic type hydrogen-ion buffering agent. Specifically, in accordance with this embodiment of the invention, tricine, N-tris-(hydroxymethyl)methyl glycine which exhibits a $pK_a$ of about 8.2, is incorporated in the culture medium. It is preferred to employ the organic buffering agent in an amount within the range of 500-1500 wppm (0.05-0.15 weight percent) with a concentration of 1000 wppm normally being adequate. Occasionally, it may be desirable to make an initial pH adjustment by the addition of a small amount of sulfuric acid.

Following the addition of the inorganic salts to the medium, it is preferred to add a portion of the methanol requirement followed by the glycerophosphate and the buffering agent, if employed. The culture is then inoculated with the microorganism. The additional methanol requirement is then added serially in time as taught in the Tannahill et al. patent. However, the alternative procedure of adding the total amount of the methanol substrate at the start of the fermentation procedure may also be followed.

To demonstrate the improvements obtained by the practice of the present invention, comparative fermentation experiments were carried out. In one suite of experiments, a culture medium was prepared by the addition to distilled water of inorganic salts in the amounts and in the order set forth in Table II.

TABLE II

| Material | Grams per Liter |
| --- | --- |
| $KH_2PO_4$ | 3.75 |
| $Na_2HPO_4$ | 2.5 |
| $NaNO_3$ | 2.5 |
| $MgSO_4 \cdot 7H_2O$ | 0.4 |
| $Fe(NH_4)_2(SO_4)_2 \cdot 6H_2O$ | 0.096 |
| $Ca(NO_3)_2 \cdot 4H_2O$ | 0.025 |
| $ZnSO_4 \cdot 7H_2O$ | 0.0032 |

NaEDTA, in the amount of 0.082 gram per liter, was added with the iron salt. Methanol and an inoculum of *Methylomonas mucosa*, obtained from a relatively active broth identified as Culture No. 1, were then added to the solution of salts. The inoculum was added to the culture medium in an amount of 10 volume percent and the methanol was added in an amount of 1.5 volume percent. In this experiment, as well as in the others described below, the culture medium was not autoclaved and the fermentation procedure was carried out over a 3-day period with an additional increment of methanol in an amount of 1.5 volume percent added at the end of the second day. In each experiment, a 1-liter Erlenmeyer flask loosely capped with a cotton plug served as the culture vessel. Throughout the growth period, the incubation temperature was maintained at 30° C. and the culture medium was agitated by placing the flask in a gyrorotary shaker. At the start of the fermentation process, and at the end of each day, the pH of the culture medium was monitored and its viscosity was measured with a Brookfield viscometer, equipped with UL adaptor, at shear rates of 1.0 and 1.7 reciprocal seconds. The fermentation procedure was then repeated in exactly the same manner as described above except that in this case the *Methylomonas mucosa* inoculum was obtained from a less active broth identified as Culture No. 2.

A second suite of growth experiments was carried out in accordance with the present invention. The experimental procedure was identical to that described above except that sodium glycerophosphate, in an amount of 12 grams per liter, was employed as a substitute for the sodium and potassium salts set forth in Table II, and tricine was added in an amount of 1 gram per liter. NaEDTA in an amount of 0.082 gram per liter was added with the iron salt similarly as in the first suite of experiments. The second suite of experiments included two runs, one carried out with the more active Culture No. 1 and the other with the less active Culture No. 2. Viscosity and pH measurements were also taken at time 0 and at the end of the first, second and third days, similarly as in the first suite of experiments.

The results of the first and second suites of experiments are set forth in Tables III and IV, respectively.

TABLE III

| Inoculum | Time (days) | pH | Viscosity (cp) at Indicated Nominal Shear Rate (Sec$^{-1}$) 1.0 | 1.7 |
|---|---|---|---|---|
| Culture No. 1 | 0 | 6.8 | 1.0 | 1.0 |
|  | 1 | 7.10 | 88. | 72.0 |
|  | 2 | 7.28 | 1400. | 840. |
|  | 3 | 7.50 | 1100. | 805. |
| Culture No. 2 | 0 | 6.8 | 1.0 | 1.0 |
|  | 1 | 7.05 | 20. | 20. |
|  | 2 | 7.10 | 780. | 560. |
|  | 3 | 7.28 | 870. | 630. |

TABLE IV

| Inoculum | Time (days) | pH | Viscosity 1.0 | 1.7 |
|---|---|---|---|---|
| Culture No. 1 | 0 | 6.8 | 1.0 | 1.0 |
|  | 1 | 7.05 | 800. | 560. |
|  | 2 | 7.12 | 2550. | 1750. |
|  | 3 | 7.20 | 3050. | 2050. |
| Culture No. 2 | 0 | 6.8 | 1.0 | 1.0 |
|  | 1 | 6.95 | 134. | 72. |
|  | 2 | 6.90 | 1300. | 810. |
|  | 3 | 6.85 | 1975. | 1290. |

As can be seen from a comparison of Tables III and IV, the fermentation process carried out in accordance with the present invention resulted in significant increase in the rate of production of biopolymer, as reflected in the viscosity of the fermenting culture, particularly during the early stage of fermentation. Further, the amount of biopolymer produced at the end of fermentation was significantly higher by the employment of the present invention. Note that during the first 24 hours of fermentation, the low shear rate viscosity of the culture medium increased about ninefold for the culture medium derived from the more active Culture No. 1 and nearly sevenfold for the culture medium derived from the less active Culture No. 2. This accelerated rate of thickening offers a significant advantage in applications such as in waterflood mobility control where it is desired to produce the polymer at the field site. In this regard, the biopolymer which is added to the injected water can be made available as a "reconstituted" material or as the in vivo form.

The reconstituted polymer may be recovered at the conclusion of the fermentation procedure by techniques well known to those skilled in the art. For example, the fermentation broth may be diluted with water and the polymer then precipitated with a mixture of water and an alcohol such as isopropanol, or through the use of a complexing agent such as a quaternary ammonium salt. Bacterial debris may be removed by any suitable means such as filtration and the polymer then dried and ground to yield the solid polymer in powdered form.

While the reconstituted material may be employed as a thickening agent in aqueous solution, there appears to be some loss in viscosity yield. For example as shown in FIG. 14 and the attendant text of the aforementioned thesis by Martin, the fermentation broth can be diluted directly to produce a viscous aqueous solution having a higher viscosity yield than solutions produced by hydration of the reconstituted polymer. The present invention is particularly well adapted to the production of the biopolymer which is then employed in the in vivo form by the addition of make-up water to the fermentation broth.

In producing the biopolymer at a field site for use in the in vivo form for mobility control applications, the viscous broth at the conclusion of the fermentation procedure can be pumped out of the fermenter to a holding tank where it is mixed with make-up water. In some cases, several dilution steps may be employed. For example the broth may be initially diluted to provide a viscosity conducive to easier handling and then centrifuged to remove unwanted biomass. Thereafter, various chemical agents such as enzymes to remove cellular debris may be employed as well as other agents such as a corrosion inhibitor, oxygen scavenger, fungicide, mold inhibitor, and a bactericide which may be added to minimize potential sources of product degradation. Thereafter, additional make-up water may be added to produce a polymer solution of the desired viscosity for mobility control purposes and the solution then introduced into a wellbore penetrating the subterranean oil reservoir.

It will also be noted that the pH measurements set forth in Tables III and IV confirm that the tests carried out in accordance with the present invention resulted in considerably less variance of the pH of the culture medium, from the optimum value of 7.0, as measured at the end of each day. Thus, Table IV shows a maximum pH variance of 0.4 unit for the more active Culture No. 1 and .15 unit for the less active Culture No. 2 as compared with maximum pH variations shown in Table III of 0.7 and 0.48 for Cultures Nos. 1 and 2, respectively.

I claim:

1. In a process for the production of a heteropolysaccharide by fermentation of a methanol containing culture medium with a microorganism of Methylomonas mucosa NRRL B-5696, the improvement comprising incorporating into said culture medium an alkali metal glycerophosphate as the predominant source of assimilable phosphate.

2. The method of claim 1 wherein said alkali metal glycerophosphate is sodium glycerophosphate.

3. The method of claim 2 wherein said sodium glycerophosphate is present in said culture medium in an amount within the range of 0.3–3.0 weight percent.

4. The method of claim 1 wherein said culture medium contains soluble iron, the improvement further comprising employing in said culture medium a chelating agent for iron selected from the group consisting of alkali metal salts of ethylenediaminetetraacetic acid and ferric/alkali metal salts of ethylenediaminetetraacetic acid.

5. The method of claim 4 wherein said chelating agent is present in said culture medium in an amount within the range of 0.0001–0.02 weight percent.

6. The method of claim 4 wherein said chelating agent comprises sodium salt of ethylenediaminetetraacetic acid.

7. The method of claim 4 wherein said chelating agent comprises ferric/sodium salt of ethylenediaminetetraacetic acid.

8. In the method of claim 1 the improvement further comprising incorporating into said culture medium an organic hydrogen-ion buffering agent.

9. The method of claim 8 wherein said hydrogen-ion buffering agent comprises N-tris-(hydroxymethyl)-methyl glycine.

10. The method of claim 9 wherein said N-tris-(hydroxymethyl)methyl glycine is present in said culture medium in an amount of 0.05–0.15 weight percent.

11. The method of claim 1 further comprising, after the fermentation process has proceeded to produce said heteropolysaccharide in a viscous fermentation broth, mixing the fermentation broth containing said heteropolysaccharide with make-up water to produce a viscous aqueous solution of said heteropolysaccharide, and introducing said aqueous viscous solution into a wellbore penetrating a subterranean oil reservoir.

* * * * *